(12) United States Patent
Falkenstein et al.

(10) Patent No.: US 10,273,277 B2
(45) Date of Patent: Apr. 30, 2019

(54) METHOD FOR PURIFYING PEGYLATED ERYTHROPOIETIN

(71) Applicant: Hoffmann-La Roche Inc., Little Falls, NJ (US)

(72) Inventors: Roberto Falkenstein, Munich (DE); Wolfgang Koehnlein, Benediktbeuern (DE); Wolfgang Kuhne, Penzberg (DE); Hartmut Schurig, Loerrach (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 15/048,689

(22) Filed: Feb. 19, 2016

(65) Prior Publication Data

US 2017/0008941 A1 Jan. 12, 2017

Related U.S. Application Data

(63) Continuation of application No. 14/090,927, filed on Nov. 26, 2013, now abandoned, which is a continuation of application No. 13/232,628, filed on Sep. 14, 2011, now abandoned.

(30) Foreign Application Priority Data

Sep. 14, 2010 (EP) .................................. 10176616

(51) Int. Cl.
| | | |
|---|---|---|
| C07K 1/18 | (2006.01) | |
| A61K 38/18 | (2006.01) | |
| A61K 47/60 | (2017.01) | |
| B01J 39/26 | (2006.01) | |
| C07K 14/505 | (2006.01) | |

(52) U.S. Cl.
CPC ........ *C07K 14/505* (2013.01); *A61K 38/1816* (2013.01); *A61K 47/60* (2017.08); *B01J 39/26* (2013.01); *C07K 1/18* (2013.01); *Y02P 20/582* (2015.11)

(58) Field of Classification Search
CPC .................................................. C07K 14/505
See application file for complete search history.

(56) References Cited

U.S. PATENT DOCUMENTS

| | | |
|---|---|---|
| 5,641,670 A | 6/1997 | Treco et al. |
| 5,733,761 A | 3/1998 | Treco et al. |
| 5,876,969 A | 2/1999 | Fleer et al. |
| 5,932,462 A | 3/1999 | Harris et al. |
| 6,583,272 B1 | 6/2003 | Bailon |
| 2002/0147311 A1 | 10/2002 | Gillies et al. |
| 2005/0008649 A1 | 1/2005 | Shin et al. |
| 2005/0114037 A1 | 5/2005 | Desjarlais et al. |
| 2005/0100991 A1 | 12/2005 | Rosen et al. |
| 2009/0118476 A1 | 5/2009 | Burg et al. |
| 2016/0333066 A1 | 11/2016 | Schmalz et al. |

FOREIGN PATENT DOCUMENTS

| | | |
|---|---|---|
| EP | 473084 | 3/1992 |
| EP | 0530447 | 10/1997 |
| EP | 0 442 724 B1 | 10/1999 |
| EP | 1 064 951 B1 | 8/2007 |
| WO | 89/05157 | 6/1989 |
| WO | 90/11354 | 10/1990 |
| WO | 91/06667 | 5/1991 |
| WO | 91/09955 | 7/1991 |
| WO | 93/09222 | 5/1993 |
| WO | 94/01451 | 1/1994 |
| WO | 94/12650 | 6/1994 |
| WO | 95/31560 | 11/1995 |
| WO | 00/44785 | 8/2000 |
| WO | 01/02017 A2 | 1/2001 |
| WO | 2004/024866 | 3/2004 |
| WO | 2006/011839 | 2/2006 |
| WO | 2006/073846 | 7/2006 |
| WO | 2007/010552 | 1/2007 |
| WO | 2009/010270 | 1/2009 |
| WO | 2009/010271 | 1/2009 |
| WO | 2010/100220 | 9/2010 |

OTHER PUBLICATIONS

US 5,733,746 A, 03/1998, Treco et al. (withdrawn)
(GE Healthcare Sephacryl High Resolution media HiPrep Sephacryl HR columns2008).
Danielsson et al., "One-step purification of monoclonal IgG antibodies from mouse ascites" J Immunol Methods 115:79-88 ( 1988).
Delgado et al. et al., "The uses and properties of PEG-linked proteins" Crit Rev Ther Drug 9(3-4):249-304 ( 1992).
Doherty et al., "Site-specific PEGylation of engineered cysteine analogues of recombinant human granulocyte-macrophage colony-stimulating factor" Bioconjugate Chem 16:1291-1298 ( 2005).
Fee et al., "PEG-proteins: Reaction engineering and separation issues" Chemical Engineering Science 61:924-939 ( 2006).
Fee et al., "Prediction of the visosity radius and the size exclusion chromatograph behavior of PEGylated proteins" Bioconjugate Chem. 15:1304-1313 ( 2004).

(Continued)

*Primary Examiner* — Paul J Holland
(74) *Attorney, Agent, or Firm* — Morrison & Foerster LLP

(57) ABSTRACT

Herein is reported a method for the purification of a protein comprising erythropoietin and a single poly (ethylene glycol) residue from reaction by-products or not reacted starting material by a cation exchange chromatography method. It has been found that by employing a cation exchange SP Sephacryl™ S 500 HR chromatography material conditioned to a conductivity of 21 mS/cm and a linear gradient elution a fusion protein of erythropoietin and a single poly (ethylene glycol) residue can be obtained in a single step with high purity and yield.

9 Claims, 7 Drawing Sheets

Specification includes a Sequence Listing.

(56) References Cited

OTHER PUBLICATIONS

Felix, Arthur M., "Site-Specific Poly(ethylene glycol)ylation of Peptides" ACS SYM SER:218-238 ( 1997).
Francis, G.E., et al., "PEGylation of cytokines and other therapeutic proteins and peptides: the importance of biological optimisation of coupling techniques" Int'l Journal of Hematology 68:1-18 ( 1998).
GE Healthcare Bio-Sciences, MacroCap SP Instructions., pp. 1-16 (2005).
Ghosh et al., "Purification of PEGylated Proteins Using ION Exchange Membrane Chromatography" Abstract 238th ACS National Meeting, Washington, D.C., pp. BIOT 186 (2009).
Gombotz et al., "PEGylation: A Tool to Enhance Protein Delivery" Other ACS Symposium Series, Washington, D.C., pp. 110-123 (2000).
Gong et al., "Discarded free PEG-based assay for obtaining the modification extent of pegylated proteins" Talanta 71 :381-384 ( 2007).
Jevsevar et al., "PEGylation of therapeutic proteins" Biotechnol. J. 5:113-128 ( 2010).
Knudson et al., "Additional studies in the separation of PEGylated proteins by reversed phase chromatography" Chromatography Online (LCGC North America) suppl.:11-13 ( 2008).
Knudson et al., "Evaluating separations of PEGylated proteins using gel filtration chromatography" Chromatography Online (LC-GC Europe):34-36 ( 2008).
Lu, Yi-An, et al. et al., "Pegylated Peptides III. Solid-phase Synthesis with Pegylating Reagents of Varying Molecular Weight: Synthesis of Multiply Pegylated Peptides" React Polym 22:221-20 ( 1994).
Molek et al., "Separation of PEGylated alph-lactalbumin from unreacted precursors and byproducts using ultrafiltration" Biotechnol. Prog. 23: 1417-1424 ( 2007).
Molek, "Separation of pegylated proteins using ultrafiltration" Abstract 232nd ACS National Meeting, San Francisco, CA, pp. BIOT-193 (2006).
Monfardini, C. et al, "A branched monomethoxypoly (ethylene glycol) for protein modification" Bioeonjugate Chem. 6:62-69 ( 1995).
Moosmann et al., "Analytical and preparative separation of PEGylated lysozyme for the characterization of chromatography media" Journal of Chromatography A 1217 :209-215 ( 2010).
Morpurgo, M. et al., "Preparation and characterization of poly(ethylene glycol) vinyl sulfone" Bioconjugate Chem. 7:363-368 ( 1996).
Nakhgevany et al., "The Pegylation and Purification of Cytochrom P-450" Abstract 211th ACS National Meeting, New Orleans, LA, pp. 186 (1996).
NCBI Database, ACJ06770. 1, May 29, 2009.
Necina et al., "Capture of human monoclonal antibodies from cellc ulture supernatant by ion exchange media exhibiting high charge density" Biotechnol Bioeng 60(6):689-698 (Dec. 20, 1998).
Pabst et al., "Comparison of strong anion-exchangers for the purification of PEGylated protein" Journal of Chromatograph A 1147:172-182 ( 2007).
Pharmeuropa Special Issue "Collaborative Study for the Establishment of a Biological Referenee Preparation for Erythropoietin" (Bio 97-2):31-48 ( 1997).
Rito-Palomares, "Bioengineering Strategies Based on Aqueous Two-phase Systems for the Separation of PEGylated from Unmodified Proteins" Abstract 239th ACS National Meeting, San Francisco, CA, pp. BIOT-338 (2010).
Rosendahl et al., "A long-acting highly potent interferon alpha-2 conjugate created using site-specific PEGylation" Bioeonjugate Chem. 16:200-207 (2005).
Seely et al., "Making site-specific PEGylation work" BioPharm International 18(3):30-41 (Mar. 2005).
Veronese, "Peptide and protein PEGylation: a review of problems and solutions" Biomaterials 22(5):405-417 (Mar. 1, 2001).
Wang et al., "High-level expression of human TFF3 in *Escherichia coli*" Peptides 26: 1213-1218 ( 2005).
Wu et al., "Site-directe PEGylation of human basic fibroblast growth factor" Protein Expression & Purification 48:24-27 ( 2006).
Yu et al., "Purification of PEGylated protein using membrane chromatography" J. of Pharmaceutical Sciences 99(8):3326 (Aug. 2010).
Yu, P. et al., "Facile purification of mono-PEGylated interleukin-1 receptor antagonist and its characterization with mult-angle laser light scattering" Process Biochemistry 42:971-977 ( 2007).
Yun, Qiang et al., "reproducible preparation and effective separation of PEGylated recombinant human granulocyte colony-stimulating factor with novel 'PEG-pellet' PEGylation mode and ion-exchange chromatography" Journal of Biotechnology 118:67-74 ( 2005).
Conversion table from CRC Handbook of Chem & Physics Electrical Conductivity of Aqueous Solutions: Downloaded Mar. 24, 2017 from http://sites.chem.colostate.edu/diverdi/all_ courses/CRC% 20reference%20data/electrical%20conductivity%20of%20aqueous% 20solutions.pdf.

A

B

C

A

B

C

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
```

```
                130                 135                 140
Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

METHOD FOR PURIFYING PEGYLATED ERYTHROPOIETIN

CROSS REFERENCE TO RELATED APPLICATIONS

This application is a Continuation of U.S. application Ser. No. 14/090,927, filed Nov. 26, 2013, now abandoned, which is a Continuation of U.S. application Ser. No. 13/232,628, filed Sep. 14, 2011, now abandoned, which claims the benefit of priority under 35 USC § 119(a) to European patent application number 10 176 616.0, filed 14 Sep. 2010, the disclosure of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Feb. 19, 2016, is named Sequence Listing.txt and is 3,289 bytes in size.

BACKGROUND OF THE INVENTION

Herein is reported a method for purifying PEGylated erythropoietin with a linear gradient elution method on a SP Sephacryl™ S 500 HR column.

BACKGROUND OF THE INVENTION

Proteins play an important role in today's medical portfolio. For human application every therapeutic protein has to meet distinct criteria. To ensure the safety of biopharmaceutical agents to humans by-products accumulating during the production process have to be removed especially. To fulfill the regulatory specifications one or more purification steps have to follow the manufacturing process. Among other things, purity, throughput, and yield play an important role in determining an appropriate purification process.

Conjugates of therapeutic proteins have been reported, for example, for polyethylene glycol (PEG) and Interleukin-6 (EP 0 442 724), for PEG and erythropoietin (WO 01/02017), for chimeric molecules comprising Endostatin and immunoglobulins (US 2005/008649), for secreted antibody based fusion proteins (US 2002/147311), for fusion polypeptides comprising albumin (US 2005/0100991; human serum albumin U.S. Pat. No. 5,876,969), for PEGylated polypeptides (US 2005/0114037), and for erythropoietin fusions.

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun. Meth. 115 (1988) 79-88. A method for purifying a polypeptide by ion exchange chromatography is reported in WO 2004/024866 in which a gradient wash is used to resolve a polypeptide of interest from one or more contaminants. In EP 0 530 447 a process for purifying IgG monoclonal antibodies by a combination of three chromatographic steps is reported. A facile purification of mono-PEGylated interleukin-1 receptor antagonist is reported by Yu, G., et al., Process Biotechnol. 42 (2007) 971-977. Wang, H., et al., Peptides 26 (2005) 1213-1218; reports the purification of hTFF3 expressed in *E. coli* by a two step cation exchange chromatography. Yun, Q., et al. (Yun, Q., et al., J. Biotechnol. 118 (2005) 67-74) report the purification of PEGylated rhG-CSF by two consecutive ion-exchange chromatography steps.

SUMMARY OF THE INVENTION

Herein is reported a method for the purification of a protein conjugate comprising erythropoietin and a single poly (ethylene glycol) residue from reaction by-products or not reacted starting material by a cation exchange chromatography method. It has been found that by employing the cation exchange chromatography material SP Sephacryl™ S 500 HR and a linear gradient elution whereby to the column a buffered solution of a defined conductivity has been applied in advance the conjugated protein comprising erythropoietin and a single poly (ethylene glycol) residue can be obtained in a single step with high purity and yield.

Thus, herein is reported as one aspect a method for obtaining a fusion protein comprising erythropoietin and a single poly (ethylene glycol) residue comprising the following steps:

a) applying a solution with a conductivity of about 21 mS/cm to a chromatography column comprising SP Sephacryl™ S 500 HR chromatography material, b) applying a solution comprising a mixture of free erythropoietin as well as fusion proteins of erythropoietin and poly (ethylene glycol) with one or more poly (ethylene glycol) residues per erythropoietin molecule to the column of a), c) applying a solution with a conductivity of about 21 mS/cm to the column and thereby recovering fusion proteins comprising two or more poly (ethylene glycol) residues, d) applying a solution with continuously and linearly increasing conductivity up to a final value of at least 60 mS/cm to the column and thereby recovering separately the fusion protein comprising erythropoietin and a single poly (ethylene glycol) residue and free erythropoietin, whereby the fusion protein comprising erythropoietin and a single poly (ethylene glycol) residue is obtained first.

In one embodiment the solution with a conductivity of about 21 mS/cm is a solution with a pH value of from pH 2.5 to pH 3.5. In one embodiment the solution with a conductivity of about 21 mS/cm is a phosphate buffered solution with a pH value of from pH 2.5 to pH 3.5.

In one embodiment the solution applied in step d) has a pH value of from pH 2.5 to pH 3.5. In one embodiment the applying a solution with continuously and linearly increasing conductivity is up to a final conductivity value of about 70.0 mS/cm.

In one embodiment the solution with continuously and linearly increasing conductivity is a solution with continuously and linearly increasing sodium chloride concentration.

In one embodiment the erythropoietin is human erythropoietin. In one embodiment the human erythropoietin has the amino acid sequence of SEQ ID NO: 01 or SEQ ID NO: 02.

In one embodiment the single poly (ethylene glycol) residue has a molecular weight of from 20 kDa to 40 kDa.

In one embodiment the solution comprising a mixture of free erythropoietin and fusion proteins of erythropoietin and poly (ethylene glycol) with one or more poly (ethylene glycol) residues per erythropoietin molecule is applied to the

DESCRIPTION OF THE INVENTION

Figure 1:
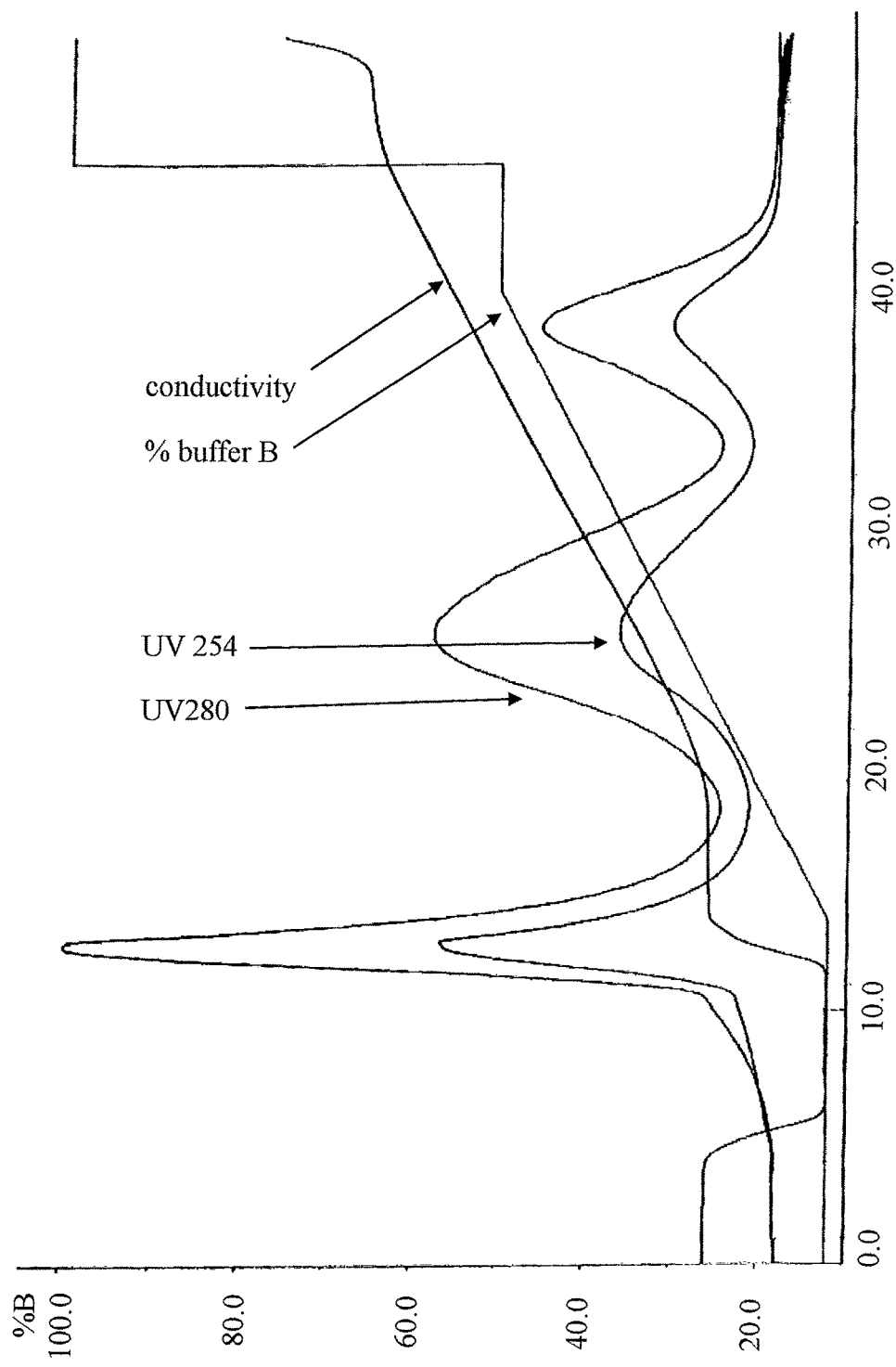
FIG. 1 Elution chromatogram of a purification of a PEGylated erythropoietin preparation with a method as reported herein.

Herein is reported a method for purifying a protein, which comprises one erythropoietin molecule and one poly (ethylene glycol) residue, with a gradient elution method, wherein the gradient is a linear conductivity gradient on a SP Sephacryl™ S 500 HR column, whereby a solution with a defined conductivity has been applied to the chromatography column prior to the application of the solution comprising the protein.

General chromatographic methods and their use are known to a person skilled in the art. See for example, Heftmann, E., (ed.), Chromatography, 5$^{th}$ edition, Part A: Fundamentals and Techniques, Elsevier Science Publishing Company, New York (1992); Deyl, Z., (ed.), Advanced Chromatographic and Electromigration Methods in Biosciences, Elsevier Science BV, Amsterdam, The Netherlands (1998); Poole, C. F., and Poole, S. K., Chromatography Today, Elsevier Science Publishing Company, New York (1991); Scopes, Protein Purification: Principles and Practice, Springer Verlag (1982); Sambrook, J., et al., (eds.), Molecular Cloning: A Laboratory Manual, Second Edition, Cold Spring Harbor Laboratory Press, Cold Spring Harbor, N.Y., (1989); or Ausubel, F. M., et al., (eds.), Current Protocols in Molecular Biology, John Wiley & Sons, Inc., New York (1987-1994).

The term "applying to" denotes a partial step of a purification method in which a solution is brought in contact with a chromatography material. This denotes that either a) the solution is added to a chromatographic device in which the chromatography material is contained, or b) that the chromatography material is added to the solution. In case a) the solution passes through the device allowing for an interaction between the chromatography material and the substances contained in the solution. Depending on the conditions, such as e.g. pH, conductivity, salt concentration, temperature, and/or flow rate, some substances of the solution bind to the chromatography material and, thus, can be recovered from the chromatography material in a further step. The substances remaining in solution can be found in the flow-through. The "flow-through" denotes the solution obtained after the passage of the device, which may either be the applied solution or a buffered solution, which is used to wash the column or to cause elution of substances bound to the chromatography material. In one embodiment the device is a column or a cassette. In case b) the chromatography material can be added, e.g. as a solid, to the solution, e.g. containing the substance of interest to be purified, allowing for an interaction between the chromatography material and the substances in solution. After the interaction the chromatography material is removed, e.g. by filtration, and substance bound to the chromatography material are also removed therewith from the solution, whereas substances not bound to the chromatography material remain in solution.

The term "bind-and-elute mode" denotes an operation mode of a chromatography step, in which a solution containing a substance of interest to be purified is applied to a chromatography material, whereby the substance of interest binds to the chromatography material. Thus, the substance of interest is retained on the chromatography material, whereas substances not of interest are removed with the flow-through or the supernatant. The substance of interest is afterwards recovered from the chromatography material in a second step with an elution solution. In one embodiment the method as reported herein is operated in bind-and-elute mode.

The solutions employed in the method as reported herein are crude or buffered solutions. The term "buffered solution" denotes a solution in which changes of pH due to the addition or release of acidic or alkaline substances is leveled by the dissolved buffer substance. Any buffer substance with such properties can be used. Generally pharmaceutically acceptable buffer substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In one embodiment the buffered solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate.

The terms "continuous elution" and "continuous elution method", which are used interchangeably within this application, denote a method wherein the conductivity of a solution causing elution, i.e. the recovery of a bound compound from a chromatography material, is changed, i.e. raised or lowered, continuously, i.e. the concentration is changed by a sequence of small steps each not bigger than a change of 2%, or of 1% of the concentration of the substance causing elution. In this "continuous elution" one or more conditions, for example the pH, the ionic strength, concentration of a salt, and/or the flow of a chromatography, may be changed linearly or exponentially or asymptotically. In one embodiment the change is linear.

The term "ion exchange chromatography material" denotes an immobile high molecular weight matrix that carries covalently bound charged substituents used as stationary phase in ion exchange chromatography. For overall charge neutrality not covalently bound counter ions are bound thereto. The "ion exchange chromatography material" has the ability to exchange its not covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g. in the case of cation exchange resins, sulfonic acid resin (S), or sulfopropyl resin (SP), or carboxymethyl resin (CM).

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "poly (ethylene glycol)" or "poly (ethylene glycol) residue" denotes a non-proteinaceous residue containing poly (ethylene glycol) as essential part. Such a poly (ethylene glycol) residue can contain further chemical groups which are necessary for binding reactions, which results from the chemical synthesis of the molecule, or which is a spacer for optimal distance of parts of the molecule. These further chemical groups are not used for the calculation of the molecular weight of the poly (ethylene glycol) residue. In addition, such a poly (ethylene glycol) residue can consist of one or more poly (ethylene glycol) chains which are covalently linked together. Poly (ethylene glycol) residues with more than one PEG chain are called multiarmed or branched poly (ethylene glycol) residues. Branched poly (ethylene glycol) residues can be prepared, for example, by the addition of polyethylene oxide to various polyols, including glycerol, pentaerythriol, and sorbitol. Branched poly (ethylene glycol) residues are reported in, for example, EP 0 473 084, U.S. Pat. No. 5,932,462. In one embodiment the poly (ethylene glycol) residue has a molecular weight of 20 kDa to 35 kDa and is a linear poly (ethylene glycol) residue. In another embodiment the poly (ethylene glycol) residue is a branched poly (ethylene glycol) residue with a molecular weight of 35 kDa to 40 kDa.

The term "fusion of erythropoietin with a poly (ethylene glycol) residue" denotes a covalent chemically introduced linkage of a poly (ethylene glycol) residue at the N-terminus or an internal lysine residue of erythropoietin. The fusion results in a protein conjugate, which comprises one erythropoietin molecule and one or more poly (ethylene glycol) residue/residues. The fusion process is also denoted as PEGylation and the product thereof as PEGylated erythropoietin. The fusion/conjugation of polypeptides with poly (ethylene glycol) residues is widely known in the state of the art and reviewed by, for example, Veronese, F. M., Biomaterials 22 (2001) 405-417. The poly (ethylene glycol) residue can be linked using different functional groups. Poly (ethylene glycols) with different molecular weight, different form, as well as different linking groups can be used (see also Francis, G. E., et al., Int. J. Hematol. 68 (1998) 1-18; Delgado, C., et al., Crit. Rev. Ther. Drug Carrier Systems 9 (1992) 249-304). The fusion of erythropoietin and a poly (ethylene glycol) residue can be performed in aqueous solution with poly (ethylene glycol) residue reagents as described, for example, in WO 00/44785. The fusion can also be performed at the solid phase according to Lu, Y., et al., Reactive Polymers 22 (1994) 221-229. Not randomly, N-terminally fusion can also be produced according to WO 94/01451.

The terms "fusing erythropoietin and poly (ethylene glycol)" and "PEGylation" denote the formation of a covalent linkage between a poly (ethylene glycol) residue at the N-terminus of the erythropoietin and/or an internal lysine residue in order to obtain a protein conjugate, which comprises one erythropoietin molecule and one poly (ethylene glycol) residue. In one embodiment PEGylation of erythropoietin is performed in aqueous solution using NETS-activated linear or branched PEG molecules of a molecular weight between 5 kDa and 40 kDa.

The term "under conditions suitable for binding" and grammatical equivalents thereof as used within this application denotes that a substance of interest, e.g. PEGylated erythropoietin, binds to a stationary phase when brought in contact with it, e.g. an ion exchange material. This does not necessarily denote that 100% of the substance of interest is bound but essentially 100% of the substance of interest is bound, i.e. at least 50% of the substance of interest is bound, at least 75% of the substance of interest is bound, at least 85% of the substance of interest is bound, or more than 95% of the substance of interest is bound to the stationary phase.

The chemical fusion or conjugation of erythropoietin and poly (ethylene glycol) generally results in a mixture of different compounds, such as poly-PEGylated erythropoietin, mono-PEGylated erythropoietin, not-PEGylated erythropoietin, hydrolysis products of the activated PEG ester, as well as hydrolysis products of the erythropoietin itself. In order to obtain a mono-PEGylated erythropoietin in substantially homogeneous form these substances have to be separated.

Therefore, it is one aspect as reported herein to provide a method for producing a protein conjugate, which comprises one erythropoietin molecule and a single poly (ethylene glycol) residue, in substantially homogenous form wherein the method comprises the following steps:
  a) conjugating erythropoietin and poly (ethylene glycol) using an activated poly (ethylene glycol) ester of a molecular weight of from 20 kDa to 40 kDa,
  b) applying the conjugates obtained in step a) to an SP Sephacryl™ S 500 HR chromatography material to which a solution with a conductivity of about 21 mS/cm has been applied,
  c) recovering the protein, which comprises one erythropoietin molecule and a single poly (ethylene glycol) residue (mono-PEGylated erythropoietin), in a substantially homogeneous form by a linear conductivity gradient elution and thereby producing the protein conjugate, which comprises erythropoietin and a single poly (ethylene glycol) residue.

In one embodiment the SP Sephacryl™ S 500 HR chromatography material is in a chromatography column. This method is especially useful for the purification of PEGylated recombinant erythropoietin, which is glycosylated, i.e. which has been produced by a mammalian cell, in one embodiment by a CHO cell, or a HEK293 cell, or a BHK cell, or a Per.C6® cell, or a HeLa cell and is afterwards chemically PEGylated.

In the first step of the method the erythropoietin is PEGylated. The poly (ethylene glycol) (PEG) polymer molecules used in the PEGylation reaction have a molecular weight of about 20 kDa to 40 kDa (the term "molecular weight" as used herein is to be understood as the mean molecular weight of the PEG because PEG as polymeric compound is not obtained with a defined molecular weight but in fact has a molecular weight distribution; the term "about" indicates that in the PEG preparations, some molecules will weigh more and some less than the indicated molecular weight, i.e the term about refers to a molecular weight distribution in which 95% of the PEG molecules have a molecular weight within +/−10% of the indicated molecular weight. For example, a molecular weight of 30 kDa denotes a range of from 27 kDa to 33 kDa).

The term "erythropoietin" and its abbreviation "EPO" refer to a protein having the amino acid sequence of SEQ ID NO: 1 or of SEQ ID NO: 2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, or BHK cells, or HeLa cells by recombinant DNA technology or by endogenous gene activation, i.e. the erythropoietin glycoprotein is expressed by endogenous gene activation, see for example U.S. Pat. Nos. 5,733,761, 5,641,670, 5,733,746, WO 93/09222, WO 94/12650, WO 95/31560, WO 90/11354, WO 91/06667, and WO 91/09955. In one embodiment the erythropoietin is human EPO. In one embodiment the human erythropoietin has the amino acid sequence set out in SEQ ID NO: 1 or SEQ ID NO: 2. In one embodiment the human erythropoietin has the amino acid sequence set out in SEQ ID NO: 1. The term "erythropoietin" also denotes variants of the protein of SEQ ID NO: 1 or of SEQ ID NO: 2, in which one or more amino acid residues have been changed, deleted, or inserted, and which has comparable biological activity as the not modified protein, such as e.g. reported in EP 1 064 951 or U.S. Pat. No. 6,583,272. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin are such that administration of the protein by injection to human patients results in bone marrow cells increasing production of reticulocytes and red blood cells compared to non-injected or control groups of subjects. The biological activity of the PEGylated erythropoietin obtained and purified in accordance with the method as reported herein can be tested by methods according to Bristow, A., Pharmeuropa Spec. Issue Biologicals BRP Erythropoietin Bio 97-2 (1997) 31-48.

Amino acid sequence variants of erythropoietin can be prepared by introducing appropriate modifications into the nucleotide sequence encoding the erythropoietin, or by peptide synthesis. Such modifications include, for example, deletions from, and/or insertions into, and/or substitutions of residues within the amino acid sequences of the erythropoietin. Any combination of deletion, insertion, and substitution can be made to arrive at the final construct, provided that the final construct possesses comparable biological activity to the human erythropoietin.

Conservative amino acid substitutions are shown in Table 1 under the heading of "preferred substitutions". More substantial changes are provided in Table 1 under the heading of "exemplary substitutions", and as described below in reference to amino acid side chain classes. Amino acid substitutions may be introduced into human erythropoietin and the products screened for retention of the biological activity of human erythropoietin.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The chemical PEGylation of erythropoietin generally result in a protein preparation comprising erythropoietin which is PEGylated at one or more ε-amino groups of lysine residues and/or at the N-terminal amino group. Selective PEGylation at the N-terminal amino acid can be performed according to Felix, A. M., et al., ACS Symp. Ser. 680 (Poly(ethylene glycol)) (1997) 218-238. Selective N-terminal PEGylation can be achieved during solid-phase synthesis by coupling of a $N^\alpha$-PEGylated amino acid derivative to the N-1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

Suitable PEG derivatives are activated PEG molecules with as in one embodiment an average molecular weight of from about 5 kDa to about 40 kDa, in another embodiment of from about 20 kDa to about 40 kDa, and in a further embodiment of about 30 kDa to about 35 kDa. The PEG derivatives can be linear or branched PEGs. A wide variety of PEG derivatives suitable for use in the preparation of PEG-protein and PEG-peptide conjugates are available.

Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone (m is in one embodiment an integer from about 450 to about 900 and R is lower alkyl, linear or branched, having one to six carbon atoms such as methyl, ethyl, isopropyl, etc. whereby methyl is preferred):

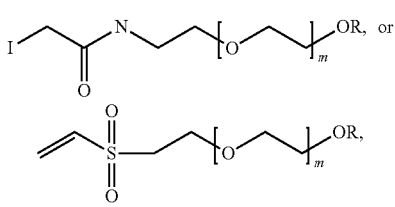

The use of these iodo-activated substances is known in the art and described e.g. by Hermanson, G. T., in Bioconjugate Techniques, Academic Press, San Diego (1996) pp. 147-148.

In one embodiment the PEG species is an activated PEG ester, e.g., N-hydroxysuccinimidyl propionate, or N-hydroxysuccinimidyl butanoate, or N-hydroxysuccinimide such as PEG-NETS (Monfardini, C., et al., Bioconjugate Chem. 6 (1995) 62-69). In one embodiment the PEG is activated by N-hydroxysuccinimide ester

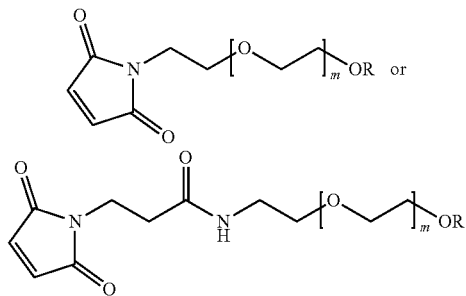

using alkoxy-PEG-N-hydroxysuccinimide, such as methoxy-PEG-N-hydroxysuccinimide (MW 30000), wherein R and m are as defined above. In one embodiment the PEG species is the N-hydroxysuccinimidyl ester of methoxy poly (ethylene glycol)-butyric acid. The term "alkoxy" refers to an alkyl ether group in which the term 'alkyl' means a straight-chain or branched-chain alkyl group containing a maximum of four carbon atoms, such as methoxy, ethoxy, n-propoxy and the like, preferably methoxy.

The term "substantially homogeneous form" denotes that the erythropoietin protein fusion or conjugate obtained, contained, or used is one having a defined number of PEG residues attached. In one embodiment the PEGylated erythropoietin is a mono-PEGylated erythropoietin. The preparation may contain unreacted (i.e., PEG group lacking) erythropoietin, poly-PEGylated erythropoietin, as well as fragments of the polypeptide generated during the PEGylation reaction. The term "substantially homogeneous form" denotes that a preparation of a mono-PEGylated erythropoietin contains at least 50% (w/w) of the mono-PEGylated erythropoietin, or at least 75% of the mono-PEGylated erythropoietin, or at least 90% of the mono-PEGylated erythropoietin, or more than 95% of the mono-PEGylated erythropoietin. The percent values are based on the area-% of the chromatogram corresponding to the chromatography method with which the mono-PEGylated erythropoietin is obtained.

Herein is reported a method for the purification of a PEGylated erythropoietin in order to obtain a substantially homogeneous form of a mono-PEGylated erythropoietin. It has been found that the chromatography material has to be condition prior to the application of the PEGylated erythropoietin preparation by a solution with a conductivity of about 21 mS/cm. If the chromatography material is conditioned with a lower conductivity the separation of the different species of the PEGylated erythropoietin preparation is less efficient. Also it is not advantageous to adjust the conductivity of the solution of the PEGylated erythropoietin preparation prior to the application to the chromatography material. Furthermore also the use of a step gradient method is less effective as not-PEGylated erythropoietin cannot be recovered quantitatively from the chromatography material. The recovery of unreacted starting material is advantageous as this can be re-used in the PEGylation reaction.

Therefore the current invention provides a method for the obtaining a mono-PEGylated erythropoietin using an SP Sephacryl™ S 500 HR chromatography material in a single step by first applying a solution with a conductivity of about 21 mS/cm to the chromatography material and afterwards applying the solution comprising the PEGylated erythropoietin preparation to the chromatography material. It has been found that the conductivity of the first solution has to be precisely controlled in order to ensure a separation of the individual components of the crude protein preparation.

Therefore, the method for obtaining a protein conjugate, which comprises erythropoietin and a single poly (ethylene glycol) residue, as reported herein comprises the following steps:
a) applying a solution with a conductivity of about 21 mS/cm to a chromatography column comprising SP Sephacryl™ S 500 HR chromatography material,
b) applying a solution comprising a mixture of free erythropoietin as well as protein conjugates of erythropoietin and poly (ethylene glycol) with one or more poly (ethylene glycol) residues per erythropoietin molecule to the column of a),
c) applying a solution with a conductivity of about 21 mS/cm to the column and thereby recovering free poly (ethylene glycol) and proteins comprising two or more poly (ethylene glycol) residues,
d) applying a solution with continuously and linearly increasing conductivity up to a final value of about 62.5 mS/cm to the column and thereby recovering separately the protein comprising erythropoietin and a single poly (ethylene glycol) residue and free erythropoietin, whereby the protein comprising erythropoietin and a single poly (ethylene glycol) residue is obtained first.

It has been found that in order to ensure a separation of the individual components of the preparation at first a solution with a conductivity of about 21 mS/cm has to be applied to the chromatography material.

In one embodiment the method is a column chromatography method.

In one embodiment prior to the applying of a solution comprising the PEGylated erythropoietin preparation a solution with a conductivity of about 21 mS/cm is applied for up to 8 column volumes to the chromatography material. In one embodiment the solution with a conductivity of about 21 mS/cm is a solution with a pH value of from pH 2.5 to pH 3.5. In one embodiment the solution with a conductivity of about 21 mS/cm is a phosphate buffered solution with a pH value of from pH 2.5 to pH 3.5.

After the application of the solution comprising the PEGylated erythropoietin preparation a solution with a conductivity of about 21 mS/cm is applied to the column and thereby free poly (ethylene glycol) and fusion proteins (i.e. protein conjugates) comprising two or more poly (ethylene glycol) residues are recovered from the chromatography material. In one embodiment the solution with a conductivity of about 21 mS/cm is applied for up to 8 column volumes to the chromatography material.

After the poly-PEGylated erythropoietin has been recovered from the chromatography material a continuous elution with a linear conductivity gradient is started. The conductivity of the mobile phase passing the chromatography material is continuously and linearly increased to at least a conductivity of about 62.5 mS/cm. In the linear gradient at first mono-PEGylated erythropoietin is recovered from the column and afterwards substantially homogeneous non-PEGylated erythropoietin is recovered. The increase in the conductivity is in one embodiment by applying a solution with an increasing sodium chloride concentration. In one embodiment the solution applied to increase the conductivity has a pH value of from pH 2.5 to pH 3.5. In one embodiment the increase of the conductivity from a value of about 21 mS/cm to the final value of at least 62.5 mS/cm is within an applied volume of the mobile phase of 10 column volumes.

In one embodiment the solution with a conductivity of about 21 mS/cm is a sodium or potassium phosphate buffered solution of about 100 mM with a pH value of about pH 3.0 with (i.e. containing) about 120 mM sodium chloride.

In one embodiment the linear gradient is a sodium chloride concentration gradient from about 120 mM to about 1000 mM sodium chloride in a sodium or potassium phosphate buffered solution of about 100 mM with a pH value of about pH 3.0.

In one embodiment the solution comprising a mixture of free erythropoietin and free poly (ethylene glycol) as well as fusion proteins (i.e. protein conjugates) of erythropoietin and poly (ethylene glycol) with one or more poly (ethylene glycol) residues per erythropoietin molecule is applied to the chromatography material that of from 1 mg/ml up to 4 mg/ml protein is applied to 1 ml of chromatography material.

The term "SP Sephacryl™ S 500 HR chromatography material" denotes a cation exchange chromatography material also denotes as MacroCap SP (both available from GE Healthcare). The SP Sephacryl™ S 500 HR chromatography material is in one embodiment a cross-linked copolymer of allyl dextran and N,N-methylene bisacrylamide with sulfonic acid as chromatographical functional group and is, thus, a strong cation exchange chromatography material.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO: 01 Amino acid sequence of human erythropoietin.

SEQ ID NO: 02 Amino acid sequence of human erythropoietin.

EXAMPLES

Materials & Methods
Analytical Size Exclusion Chromatography:
resin: TSK 3000 (Tosohaas)
column: 300×7.8 mm
flow rate: 0.5 ml/min
elution solution: 200 mM potassium phosphate containing 250 mM potassium chloride, adjusted to pH 7.0
wavelength: 220 nm PEGylated Erythropoietin Chromatography:
resin: SP Sephacryl™ S 500 HR
bed volume: 2.5 ml
sample loading: mg/ml resin—variable (see examples below)
flow rate: 0.5 ml/min
solutions: A: 100 mM potassium phosphate, adjusted to pH 3.0
B: 100 mM potassium phosphate, 1000 mM sodium chloride, adjusted to pH 3.0
application solution: 88% A and 12% B
wash solution: 88% A and 12% B
wash volume: 20 ml (8 column volumes (CV))
linear gradient elution solution: 100% B
linear gradient: within 25 ml (10 column volumes) to 50% B
wavelength: 254 nm, 280 nm Example 1

Chromatography of a PEGylated Erythropoietin Preparation with a SP-Sephacryl™ Chromatography Material with Conditioning with a Solution with a Conductivity of About 21 mS/cm The PEGylated Erythropoietin Chromatography was performed as outlined in the Materials and Methods section.

Figure 2:
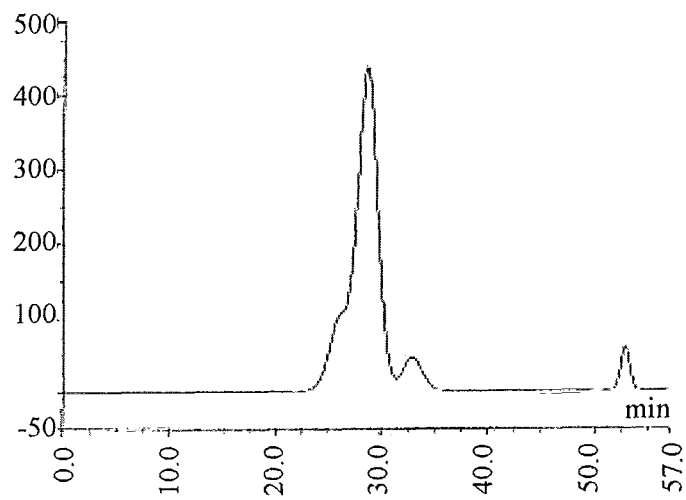
FIG. 2 SEC analytical chromatograms of the peak fractions 1, 2 and 3 of FIG. 1.
Figure 2:
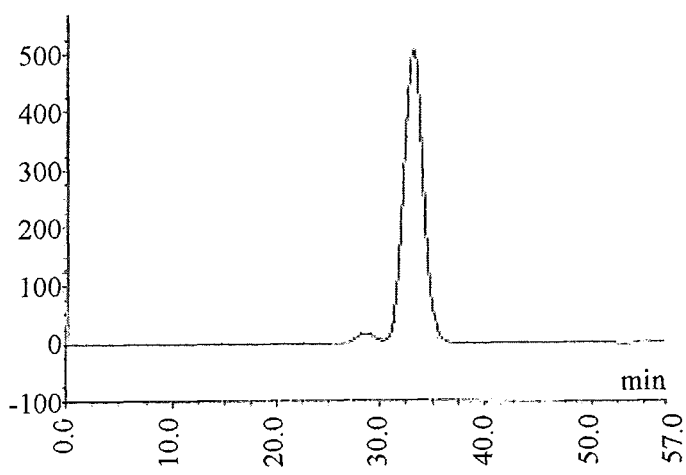
Figure 2:
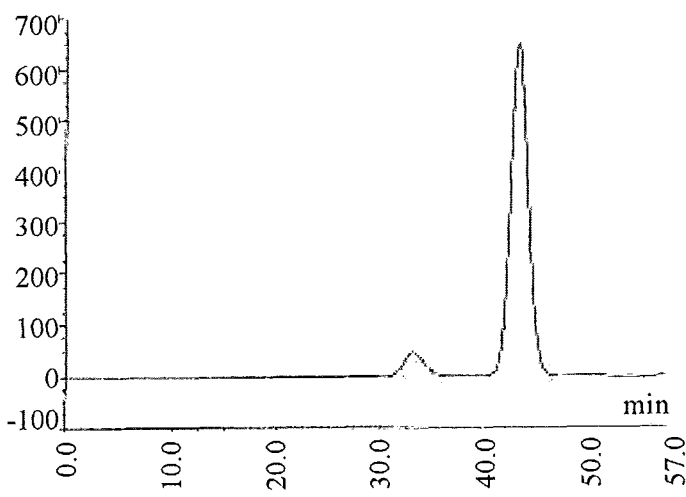

The elution chromatogram for this method is shown in FIG. 1. The analytical size exclusion chromatograms of the oligo-PEGylated erythropoietin peak fraction 1 and the mono-PEGylated peak fraction 2 and non-PEGylated peak fraction 3 is shown in FIG. 2A-C.

TABLE 2

| erythropoietin species | linear peak (peak fraction 1) [%] | gradient peak 1 (peak fraction 2) [%] | gradient peak 2 (peak fraction 3) [%] |
|---|---|---|---|
| oligo-PEGylated | 92.2 | 12.1 | 0.1 |
| mono-PEGylated | 7.8 | 87.7 | 7.3 |
| non-PEGylated | — | 0.2 | 92.6 |

Example 2

Figure 3:
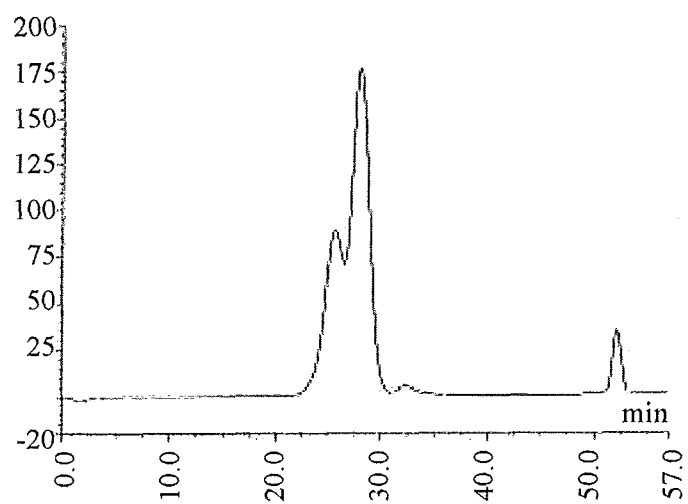
FIG. 3 SEC analytical chromatograms of the peak fractions 1, 2 and 3 of a separation wherein the chromatography column has been conditioned with a solution with higher conductivity.
Figure 3:
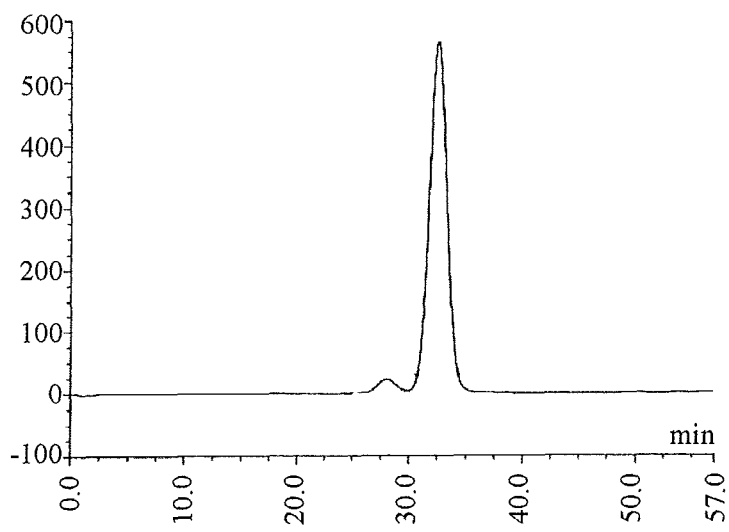
Figure 3:
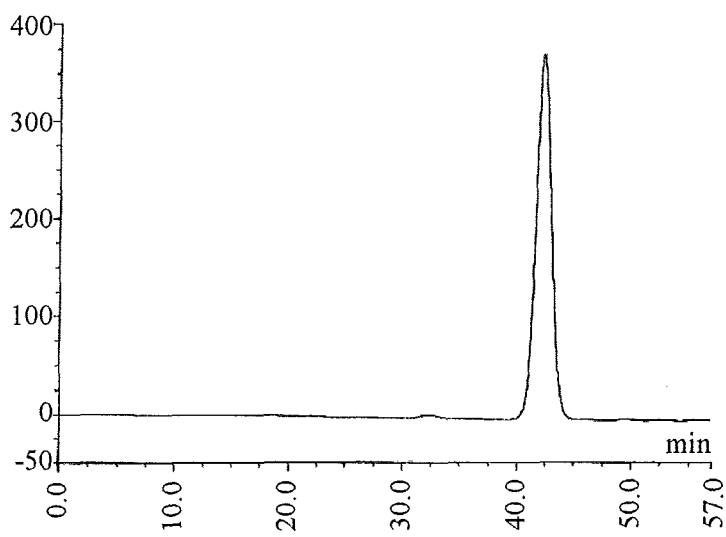

Chromatography of a PEGylated Erythropoietin Preparation with a SP-Sephacryl™ Chromatography Material with Conditioning with a Solution with a Conductivity of About 29 mS/cm The PEGylated Erythropoietin Chromatography was performed as outlined in the Materials and Methods section with the following differing parameters:
application solution: 80% A and 20% B
wash solution: 80% A and 20% B
wash volume: 20 ml (8 column volumes (CV))
linear gradient elution buffer: 100% B
linear gradient: within 25 ml (10 column volumes) to 50% B The analytical size exclusion chromatograms of the oligo-PEGylated erythropoietin peak fraction 1 and the mono-PEGylated peak fraction 2 and non-PEGylated peak fraction 3 is shown in FIG. 3A-C.

TABLE 3

| erythropoietin species | linear peak (peak fraction 1) [%] | gradient peak 1 (peak fraction 2) [%] | gradient peak 2 (peak fraction 3) [%] |
| --- | --- | --- | --- |
| oligo-PEGylated | 98.0 | 18.5 | — |
| mono-PEGylated | 2.0 | 81.5 | 7.0 |
| non-PEGylated | — | — | 93.0 |

Example 3

Chromatography of a PEGylated Erythropoietin Preparation with a SP-Sephacryl™ Chromatography Material with Conditioning with a Solution with a Conductivity of About 21 mS/cm and Step Elution with a Solution with a Conductivity of 37 mS/cm The PEGylated Erythropoietin Chromatography was performed as outlined in the Materials and Methods.

Figure 4:
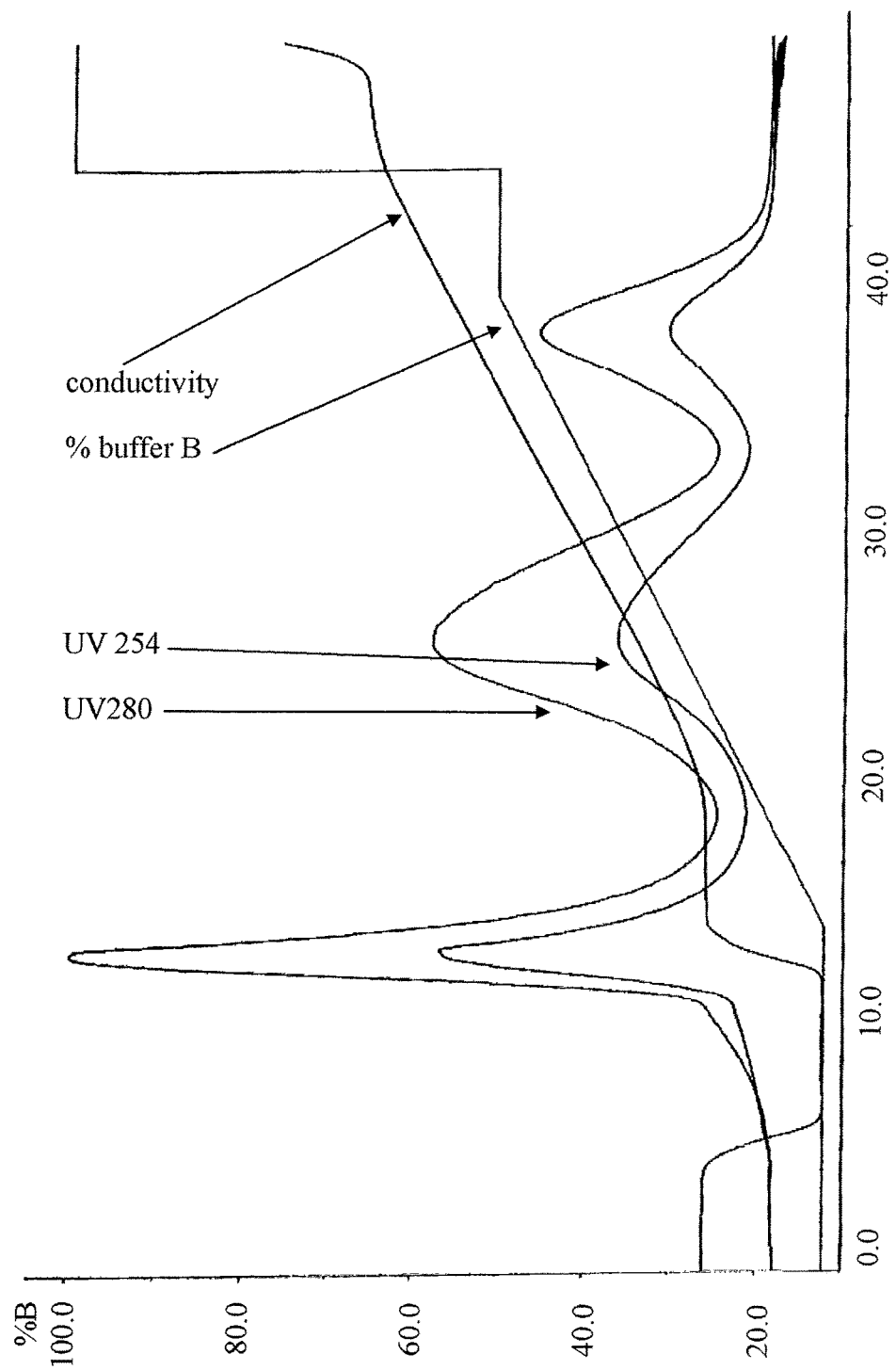
FIG. 4 Elution chromatogram of a purification of a PEGylated erythropoietin preparation with a step elution method.
Figure 5:
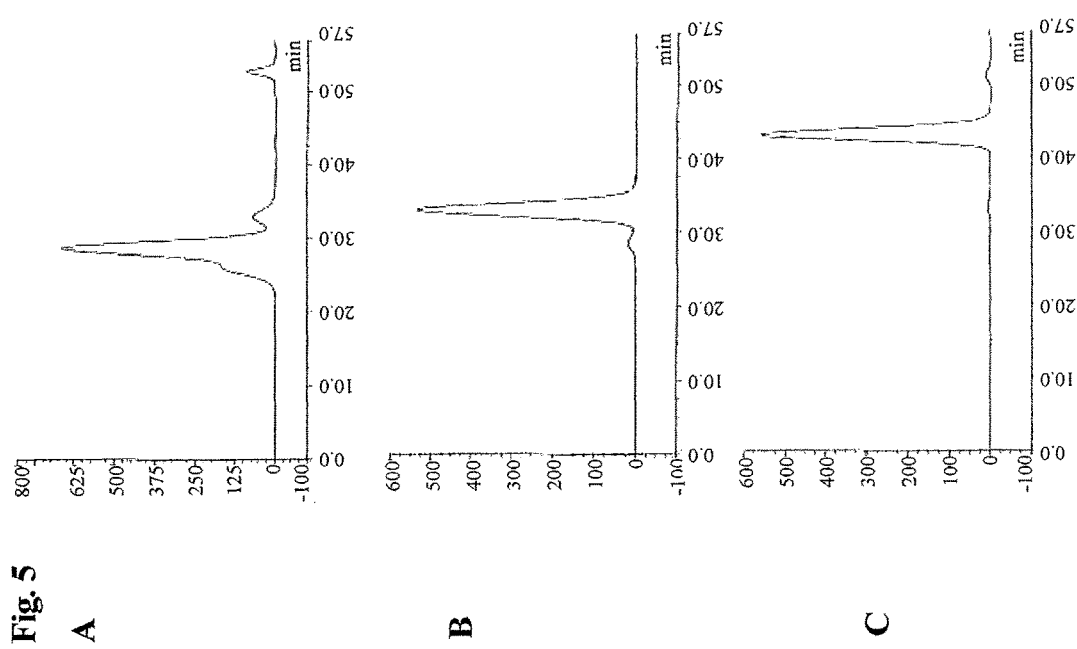
FIG. 5 SEC analytical chromatograms of the peak fractions 1, 2 and 3 (regeneration peak) of FIG. 4.

The elution chromatogram for this method is shown in FIG. 4. The analytical size exclusion chromatograms of the oligo-PEGylated erythropoietin peak fraction 1 and the mono-PEGylated peak fraction 2 and non-PEGylated peak fraction 3 is shown in FIG. 5A-C. It has to be pointed out that non-PEGylated erythropoietin could only be recovered during the regeneration of the column and not with the step elution method.

TABLE 4

| erythropoietin species | starting material [%] | linear peak (peak fraction 1) [%] | step peak 1 (peak fraction 2) [%] | column regeneration peak (peak fraction 3) [%] |
| --- | --- | --- | --- | --- |
| oligo-PEGylated | 34.8 | 92.1 | 2.7 | — |
| mono-EGylated | 45.3 | 7.7 | 96.1 | 1.4 |
| non-PEGylated | 19.9 | 0.2 | 1.2 | 98.6 |

Example 4

Chromatography of a PEGylated Erythropoietin Preparation with a SP-Sephacryl™ Chromatography Material with Conditioning with a Solution with a Conductivity of About 21 mS/cm and Sample Adjusted to a Conductivity of 20 mS/cm The PEGylated Erythropoietin Chromatography was performed as outlined in the Materials and Methods.

Figure 6:
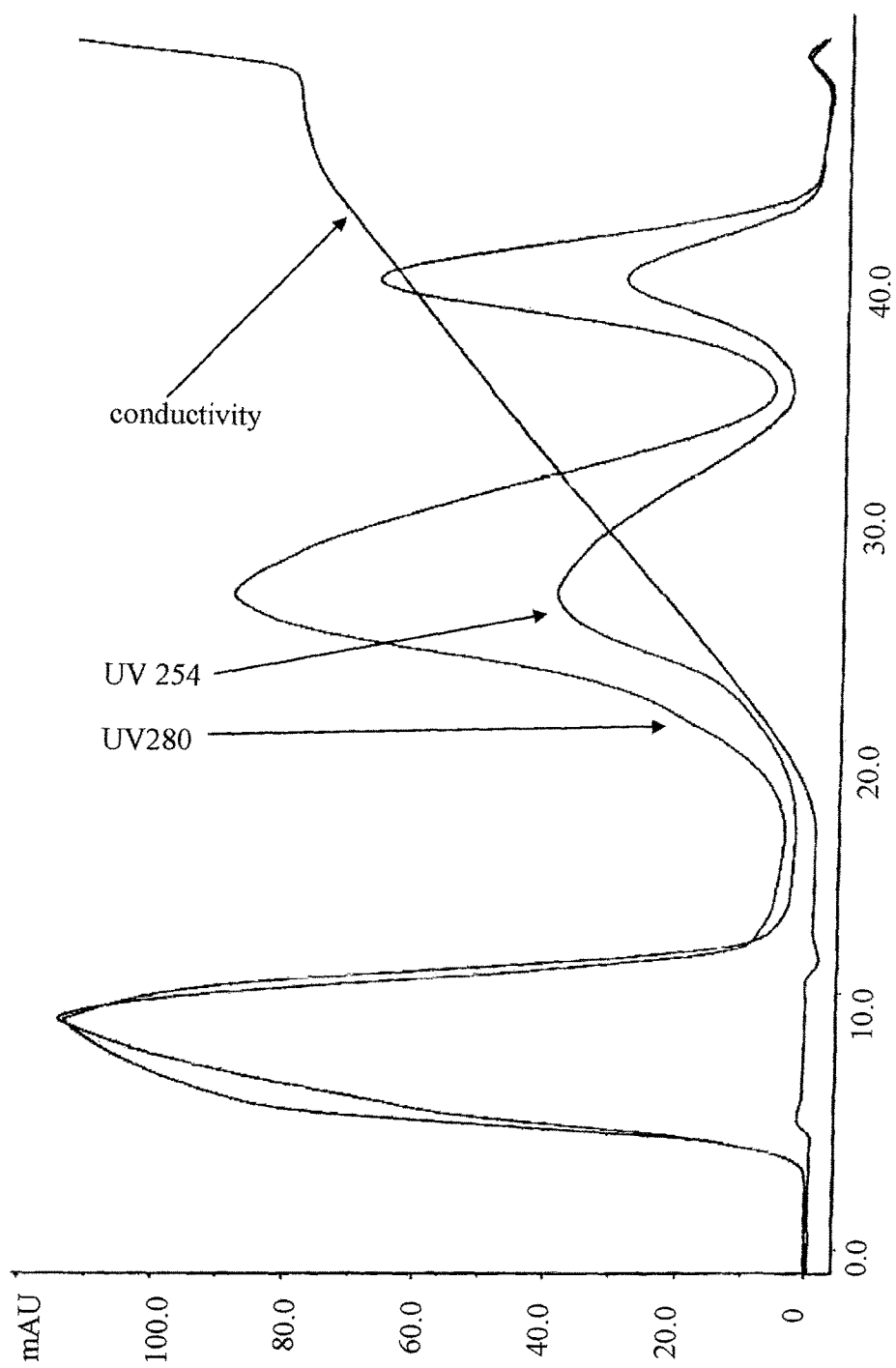
FIG. 6 Elution chromatogram of a purification of a PEGylated erythropoietin preparation with a method as reported herein with prior adjusting the conductivity of the sample solution to 20 mS/cm.
Figure 7:
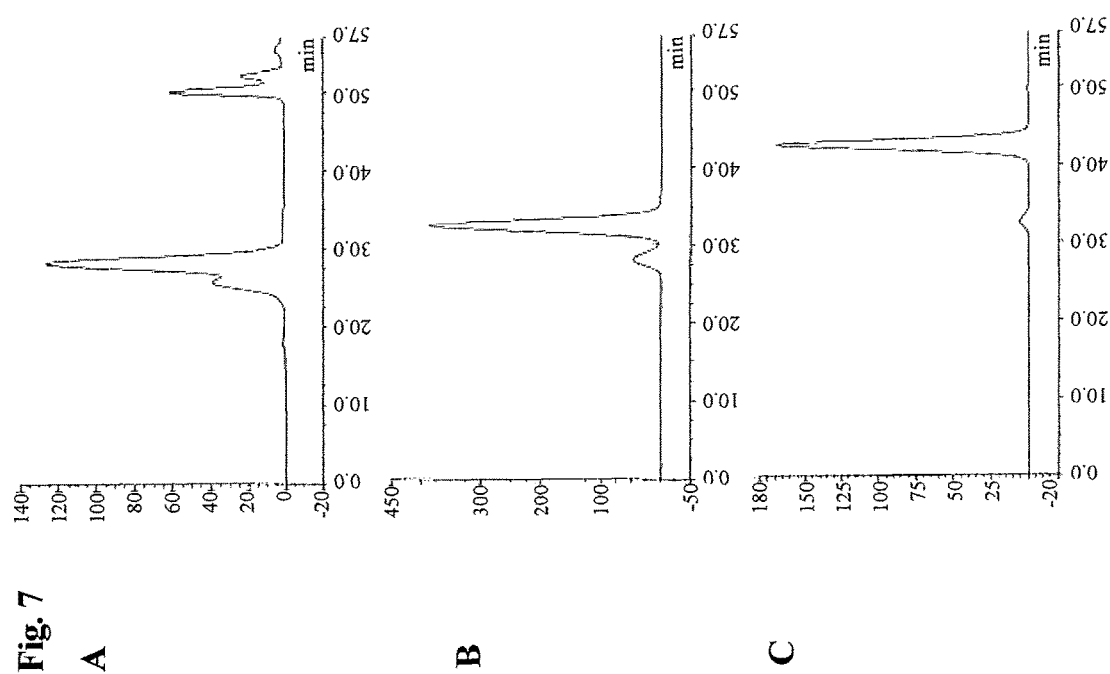
FIG. 7 SEC analytical chromatograms of the peak fractions 1, 2 and 3 of FIG. 6.

The elution chromatogram for this method is shown in FIG. 6. The analytical size exclusion chromatograms of the oligo-PEGylated erythropoietin peak fraction 1 and the mono-PEGylated peak fraction 2 and non-PEGylated peak fraction 3 is shown in FIG. 7A-C.

TABLE 5

| erythropoietin species | linear peak (peak fraction 1) [%] | gradient peak 1 (peak fraction 2) [%] | gradient peak 2 (peak fraction 3) [%] |
| --- | --- | --- | --- |
| oligo-PEGylated | 100 | 14.5 | — |
| mono-PEGylated | — | 85.3 | 3.9 |
| non-PEGylated | — | 0.1 | 96.1 |

The invention claimed is:

1. A chromatography method for obtaining a protein, which comprises erythropoietin and a single poly (ethylene glycol) residue, comprising:
   a) applying a solution comprising a mixture of erythropoietin and conjugates of erythropoietin and poly (ethylene glycol) with one or more poly (ethylene glycol) residues per erythropoietin molecule to a column comprising SP Sephacryl ™ S 500 HR chromatography material, to which a solution with a conductivity of 21 mS/cm has been applied,
   b) applying a solution with a conductivity of 21 mS/cm to the column and thereby recovering free poly (ethylene glycol), and proteins comprising two or more poly (ethylene glycol) residues, and
   c) applying a solution with linearly increasing conductivity up to a final value of 62.5 mS/cm to the column and thereby recovering separately the protein, which comprises erythropoietin and a single poly (ethylene glycol) residue, and erythropoietin, whereby the protein comprising erythropoietin and a single poly (ethylene glycol) residue is recovered first,
   wherein the protein comprising erythropoietin and a single poly (ethylene glycol) is purified after one single chromatography step.

2. The method of claim 1, wherein the solution with a conductivity of 21 mS/cm is a solution with a pH value of from pH 2.5 to pH 3.5.

3. The method of claim 1, wherein the solution with a conductivity of 21 mS/cm is a phosphate buffered solution with a pH value of from pH 2.5 to pH 3.5.

4. The method of claim 1, wherein the solution comprising a mixture of erythropoietin and conjugates of erythropoietin and poly (ethylene glycol) with one or more poly (ethylene glycol) residues per erythropoietin molecule is not adjusted to a conductivity of 21 mS/cm.

5. The method of claim 1, wherein the solution with linearly increasing conductivity is a solution with linearly increasing sodium chloride concentration.

6. The method of claim 1, wherein the solution with linearly increasing conductivity has a pH value of from pH 2.3 to pH 3.5.

7. The method of claim 1, wherein the erythropoietin is human erythropoietin.

8. The method according to claim 7, wherein the human erythropoietin has the amino acid sequence of SEQ ID NO: 1 or SEQ ID NO: 2.

9. The method of claim 1, wherein the single poly(ethylene glycol) residue has a molecular weight of from 20 kDa to 40 kDa.

* * * * *